(12) United States Patent
Lointier et al.

(10) Patent No.: US 8,075,582 B2
(45) Date of Patent: Dec. 13, 2011

(54) MULTIPLE-POUCH INTRAGASTRIC BALLOONS, SURGICAL DEVICE FOR EXPANDING SAID BALLOON AND METHOD FOR MAKING SAME

(75) Inventors: Patrice Henri Lointier, Chamalieres (FR); Roger-Michel Bory, Miribel (FR)

(73) Assignee: Compagnie Europeenne d'Etude et de Recherche de Dispositifs pour l'Implantation Par Laparoscopie, Vienne Cedex (FR)

( * ) Notice: Subject to any disclaimer, the term of this patent is extended or adjusted under 35 U.S.C. 154(b) by 1411 days.

(21) Appl. No.: 10/500,228

(22) PCT Filed: Dec. 30, 2002

(86) PCT No.: PCT/FR02/04589
§ 371 (c)(1),
(2), (4) Date: Sep. 25, 2006

(87) PCT Pub. No.: WO03/055420
PCT Pub. Date: Jul. 10, 2003

(65) Prior Publication Data
US 2007/0118168 A1    May 24, 2007

(30) Foreign Application Priority Data
Dec. 28, 2001  (FR) ...................................... 01 17102

(51) Int. Cl.
*A61M 29/00*    (2006.01)
(52) U.S. Cl. ..................................... 606/192; 623/23.67
(58) Field of Classification Search .................. 606/151, 606/153, 157; 623/23.64–23.68, 23.7; 604/7, 604/8
See application file for complete search history.

(56) References Cited

U.S. PATENT DOCUMENTS

| | | | | |
|---|---|---|---|---|
| 3,238,157 A | * | 3/1966 | Smith | 521/61 |
| 4,607,618 A | | 8/1986 | Angelchik | 128/1 R |
| 4,696,288 A | | 9/1987 | Kuzmak et al. | 128/1 R |
| 4,739,758 A | | 4/1988 | Lai et al. | 128/303 |
| 5,084,061 A | * | 1/1992 | Gau et al. | 606/195 |
| 5,234,454 A | | 8/1993 | Bangs | 606/191 |
| 4,694,827 A | | 11/1997 | Bonutti | 600/204 |
| 5,800,486 A | * | 9/1998 | Thome et al. | 607/105 |

* cited by examiner

*Primary Examiner* — Kevin T Truong
(74) *Attorney, Agent, or Firm* — Thomas, Kayden, Horstemeyer & Risley, LLP

(57) ABSTRACT

The invention relates to an expandable intra-gastric balloon (1) for treating obesity, the balloon being for implanting in the stomach in order to reduce its volume, said balloon (1) comprising a first flexible pouch (2) provided with first connection means (3) for receiving a connection member (6) that is for connection to a first fluid source in order to expand said first pouch (2) in the stomach by filling it with fluid, the balloon being characterized in that it includes at least one second flexible pouch (20) provided with second connection means (3'), said second connection means (3') being separate from the first connection means (3) in such a manner as to be capable of being connected to a second fluid source different from the first fluid source. The invention applies to treating obesity.

2 Claims, 8 Drawing Sheets

FIG. 2

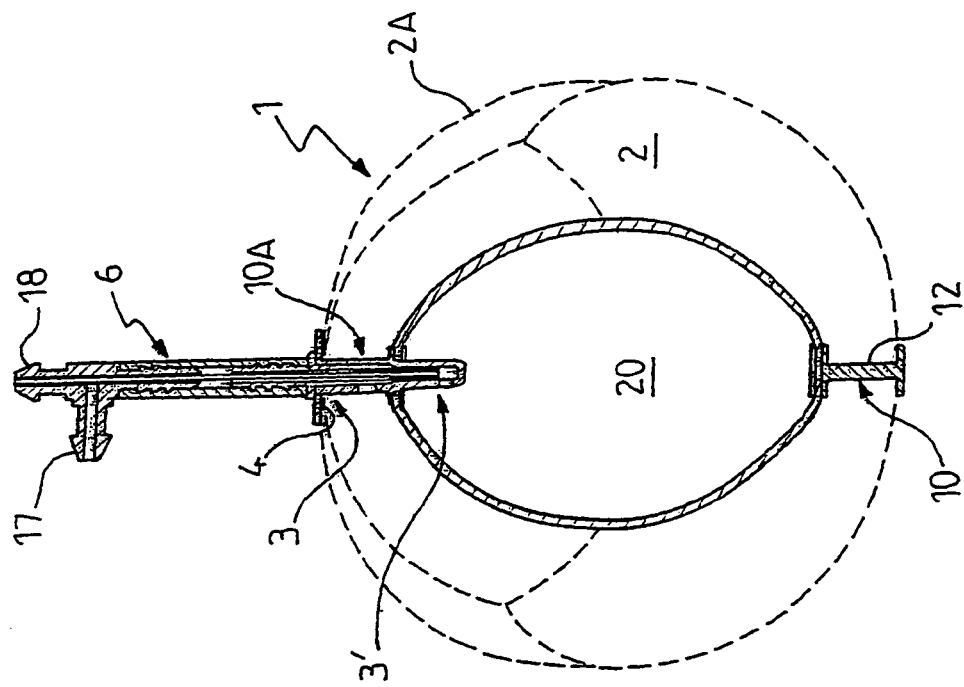
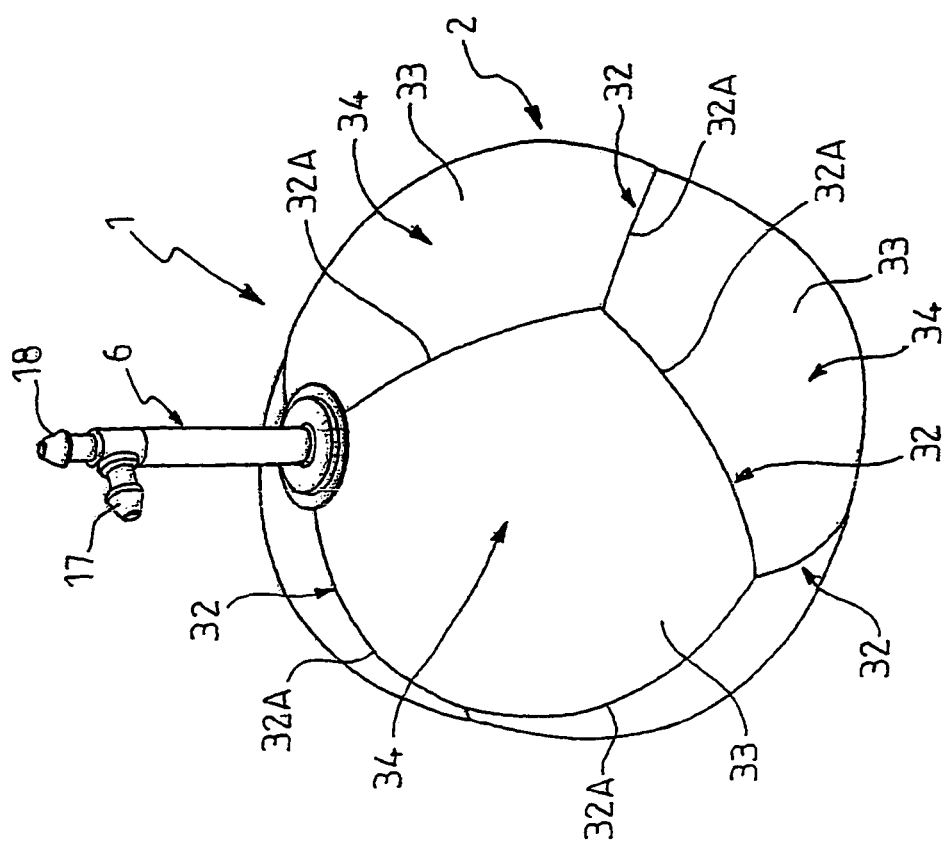

MULTIPLE-POUCH INTRAGASTRIC BALLOONS, SURGICAL DEVICE FOR EXPANDING SAID BALLOON AND METHOD FOR MAKING SAME

CROSS-REFERENCE TO RELATED APPLICATIONS

This application is a national stage application of International Application No. PCT/FR02/04589, filed Dec. 30, 2002, which claims priority to FR 01/17102, filed Dec. 28, 2001, both applications of which are hereby incorporated by reference in their entirety into the present application.

TECHNICAL FIELD

The present invention relates to the technical field of artificial devices for treating obesity, in particular morbid obesity, and most particularly it relates to devices that consist in artificially reducing the volume of the gastric cavity in order to cause the patient to feel sated quickly.

The present invention relates to an expandable intra-gastric balloon for treating obesity, for implanting in the stomach of a patient to reduce the volume of the stomach, said balloon comprising a first flexible pouch defining a predetermined inside volume, said first flexible pouch being provided with first connection means including an orifice and a valve for receiving a connection member, itself for connection to a first fluid source in order to act, after the balloon has been implanted, to expand said first pouch in the stomach by filling it with the fluid.

In completely independent manner, the invention also provides an intra-gastric balloon for treating obesity, for implanting in the stomach of a patient in order to reduce the volume of the stomach, said balloon comprising an outside wall for coming into contact with the wall of the stomach, the balloon subdividing the stomach into an upstream zone and a downstream zone in order to constitute a barrier for the passage of food between these two zones, the outside wall being shaped so as to co-operate with the wall of the stomach to define channels for passing food from the upstream zone to the downstream zone.

The invention also provides an intra-gastric balloon for treating obesity, for implanting in the stomach of a patient to reduce the volume of the stomach, said balloon comprising a flexible envelope defining a predetermined inside volume, said flexible envelope being made of an elastomer material.

Likewise in independent manner, the invention provides a method of fabricating an intra-gastric balloon for treating obesity, said balloon being for implanting in the stomach of a patient in order to reduce the volume of the stomach.

PRIOR ART

In order to treat patients suffering from obesity, in particular those presenting a weight/size ratio that does not require recourse to invasive surgical devices and methods that are expensive and traumatizing, such as surgically implanting a gastric band forming a ring around the stomach, or likewise for treating patients in which excessive overweight is itself considered as constituting a risk in the event of surgery, it is known to implant a foreign body directly in the stomach of the patient, the volume of the foreign body being sufficient to reduce the space available for food, while also reducing the rate at which food passes through the stomach.

Such foreign bodies are implanted orally, and are generally in the form of a so-called "intra-gastric" balloon constituted by a flexible pouch made of biocompatible elastomer material and implanted directly in the patient's stomach.

The balloon presents an orifice in which there is installed a valve, these two elements forming connection means into which, prior to implanting the balloon in non-expanded state, the surgeon-inserts a connection member, generally a catheter connected to a source of fluid (physiological liquid), so as to be able to inflate or expand the balloon inside the stomach.

Such intra-gastric balloons are well known, and although they provide results that are advantageous in terms of weight loss, given that they reduce the rate at which food passes through the stomach and that they contribute effectively to quickly giving the patient a sensation of being sated, they nevertheless suffer from drawbacks that are not negligible.

In particular, they often turn out to be difficult for patients to accept because of the large weight of the balloon, which encloses a significant volume of liquid, of the order of 600 milliliters (mL).

Furthermore, they can sometimes be difficult to put into place, and indeed they can also be difficult to expand and to manipulate.

Finally, it has been found that the outside shape of previously-known intra-gastric balloons is not suitable for blocking the passage of food into the remainder of the digestive tract in a manner that is sufficient and for a duration that is consequential, even though the specific purpose of such a balloon is to prolong the sensation of being sated as long as possible.

SUMMARY OF THE INVENTION

Consequently, the objects of the invention seek to remedy the various drawbacks set out above and to propose a novel expandable intra-gastric balloon for treating obesity, for implanting in the stomach of a patient, and which is of sufficient volume while nevertheless being particularly light in weight and well accepted by the patient.

Another object of the invention seeks to propose a novel intra-gastric balloon which is particularly well balanced while it is being expanded radially, and which is easy to implant.

Another object of the invention is to propose a novel intra-gastric balloon which can be implanted in particularly simplified and rapid manner, particularly during expansion.

Another object of the invention is to propose a novel intra-gastric balloon that is particularly strong and from which fluid loss is small.

Another object of the invention is to propose a novel balloon of simplified design that presents good strength generally, in particular mechanically.

Another object of the invention is to propose a novel intra-gastric balloon making it possible significantly to increase the extent to which food is blocked in the stomach.

Another object of the invention also seeks to propose a novel surgical device for treating obesity, enabling the balloon to be expanded in particularly simplified and rapid manner towards its predetermined operating volume.

Another object of the invention seeks to propose a novel method of fabricating an intra-gastric balloon which is particularly simple and effective to implement, while enabling a balloon to be obtained that presents excellent leaktightness.

The objects given to the invention are achieved by an expandable intra-gastric balloon for treating obesity, for implanting in the stomach of a patient to reduce the volume of the stomach, said balloon comprising a first flexible pouch defining a predetermined inside volume, said first flexible pouch being provided with first connection means including an orifice and a valve for receiving a connection member for connection to a first fluid source in order to expand said first pouch in the stomach by filling it with the fluid, the balloon being characterized in that it includes at least one second flexible pouch of predetermined volume and provided with second connection means with an orifice and a valve, said second connection means being separate from the first connection means so as to be capable of being connected to a second fluid source different from the first fluid source.

The objects given to the invention are also achieved by a surgical device for treating obesity, the device serving to expand an intra-gastric balloon of the invention in the stomach of a patient, the balloon comprising a first pouch and a second pouch disposed inside the first pouch, the pouches having respective orifices arranged to receive a common connection member, said device comprising a tubular connection member suitable for being inserted in a hollow central duct of the common connection means of the intra-gastric balloon, said member being provided with two independent channels each having a respective end opening out in register with a corresponding one of two holes in the central duct, and each having its opposite end connected to a respective independent endpiece suitable for being connected to distinct filler fluid sources.

The objects given to the invention are also achieved by a method of fabricating an intra-gastric balloon comprising a first pouch and a second pouch disposed inside the first pouch, the pouches having respective orifices arranged to receive a common connection member, in which method, the following steps are performed:

fabricating first and second pouches by injecting elastomer material in a mold to obtain at least two pouches each having a respective orifice, the first pouch being of dimensions greater than those of the second pouch; and during the step of fabricating the first pouch or thereafter, placing a spacer on the outside face of the first pouch substantially opposite from its orifice, the spacer presenting a free outer base plate; then bonding the two pouches together at the free outer base plate by using adhesive between said base plate and the outside face of the second pouch, substantially opposite from its orifice; and then turning the first pouch inside out, causing the second pouch to penetrate therein via its orifice.

BRIEF DESCRIPTION OF THE DRAWINGS

Other objects and advantages of the invention will appear better on reading the following description, and also from the accompanying drawings, given purely by way of non-limiting illustration, and in which:

FIG. 1 is a perspective view of an intra-gastric balloon in accordance with the invention in its maximally-expanded position, and fitted with a tubular connection member;

FIG. 2 is a longitudinal cross-section view identical to that of FIG. 1, showing an intra-gastric balloon in accordance with the invention;

BEST MANNER OF PERFORMING THE INVENTION

Figure 3:
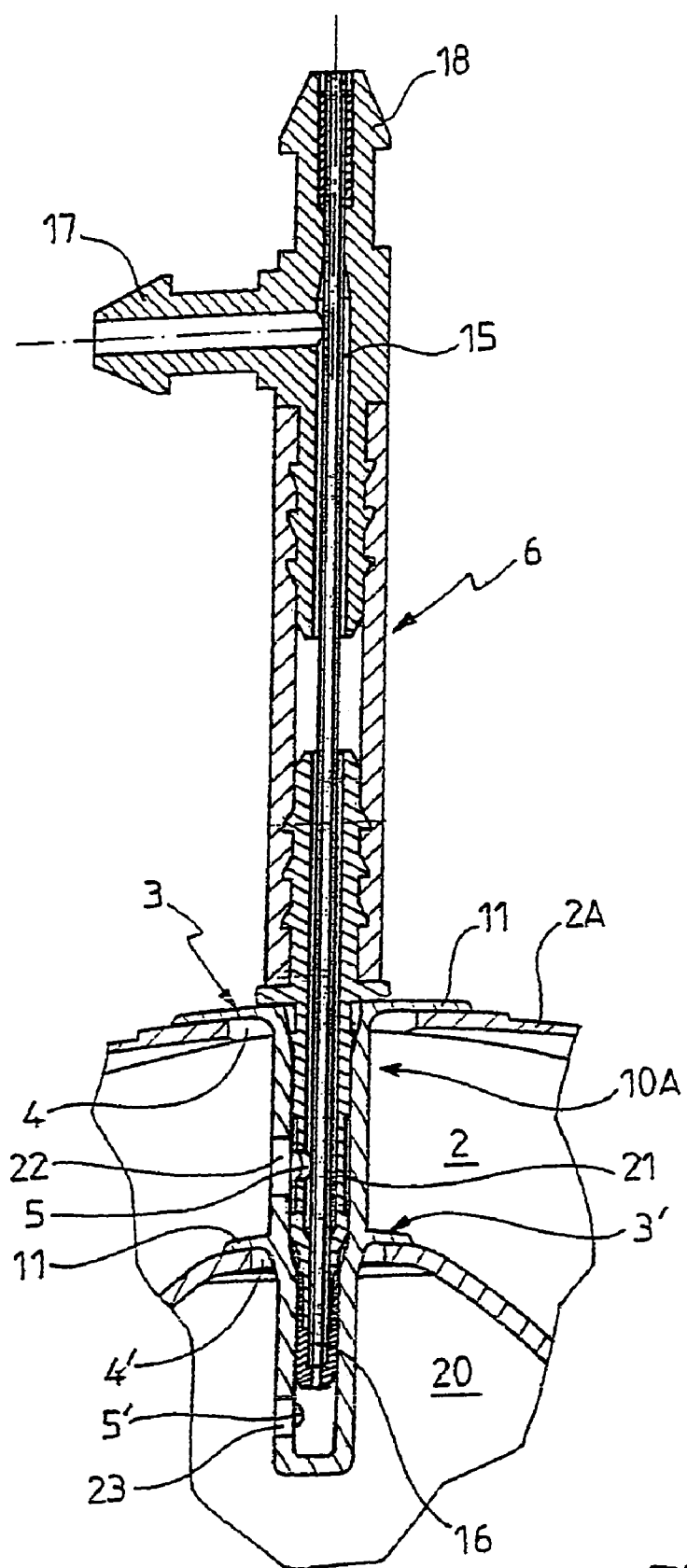
FIG. 3 is a fragmentary longitudinal cross-section view showing an implementation and assembly detail of a tubular connection member in accordance with the invention, inserted in an intra-gastric balloon in accordance with the invention.

FIGS. 1 to 6 show an intra-gastric balloon 1 in accordance with the invention, together with details of its implementation, such a balloon being designed for treating obesity and being for implanting in the stomach of a patient to reduce the volume of the stomach, insofar as it occupies a major fraction of the space available for food.

The intra-gastric balloon 1 in accordance with the invention is expandable, i.e. it is made out of flexible materials, e.g. elastomer materials, enabling it to occupy firstly a folded or slack configuration (not shown in the figures) in which it occupies a small volume that makes it easier to implant, and secondly, by using an inflation fluid, an expanded configuration of predetermined volume, e.g. about 600 mL, corresponding to its volume in use, as shown in particular in FIGS. 1 and 2.

As a general rule, an intra-gastric balloon in accordance with the invention is implanted in a manner that is conventional and well known to the person skilled in the art by passing the balloon via the mouth and the esophagus while the balloon is in its folded or slack state, and then expanding the balloon, with the balloon being put into place and prevented from moving at the end of the surgical operation once the intra-gastric balloon 1 has been positioned properly in the stomach of the patient.

The intra-gastric balloon 1 in accordance with the invention comprises a first flexible pouch 2 having outside walls 2A that define a predetermined inside volume, said first flexible pouch 2 being provided with first connection means 3 including an orifice 4 and a valve 5 for the purpose of receiving a connection member 6 that is for connection to a first source of fluid (not shown in the figures), in order to enable said first pouch 2 to be expanded in the stomach by being filled with said fluid.

According to an important characteristic of the invention, and as shown in FIGS. 1 to 6, the expandable intra-gastric balloon 1 in accordance with the invention includes at least one second flexible pouch 20 of likewise predetermined volume and provided with second connection means 3' having an orifice 4' and a valve 5', said second connection means 2' being separate and distinct from the first connection means 3 so as to be capable of being connected to a second source of fluid (not shown in the figures) that is different from the first source of fluid.

By means of this disposition, and the separation and independence of the two connection means 3 and 3' corresponding likewise to independence of the two internal volumes of the pouches 2 and 20, it is possible to expand and implant each of the pouches 2 and 20 using fluids that are different, and thus of densities that are different.

Consequently, for the same total volume of the intra-gastric balloon 1, and for equal outside volume comparable to known devices, it is possible to obtain smaller weight for the intra-gastric balloon 1 in accordance with the invention, compared with prior art balloons.

This disposition thus makes it possible to reduce the total weight of the intra-gastric balloon while it is implanted in the stomach of the patient, thereby improving the tolerance of the organism to the balloon, and also reducing side effects.

It is thus possible to inflate one of the pouches with a physiological liquid, while the other pouch is inflated with a gas of lower density, e.g. air.

In a preferred variant of the invention, as shown in FIGS. 1 to 6, the intra-gastric balloon 1 in accordance with the invention is advantageously constituted by two pouches 2 and 20 so as to form a two-pouch balloon, it being understood that within the meaning of the invention, some greater number of pouches (e.g. 3, 4, or even more pouches) could be provided without thereby going beyond the ambit of the invention, each pouch being for inflation with a different fluid.

In a first variant embodiment (not shown), the pouches 2 and 20 may be adjacent each other, being interconnected via a common face, e.g. by means of adhesive, with the balloon being formed by the combination of the pouches.

In another version of the invention that is particularly advantageous, and as shown in FIGS. 1 to 6, the intra-gastric balloon 1 of the invention includes at least one second pouch 20 which is disposed inside the first pouch 2, and which is therefore of smaller outside volume, the first pouch 2 thus being of greater dimensions, at least in the expanded state.

In this preferred variant, the second pouch 20 thus forms an internal pouch of shape that is generally identical to, but which could be different from, the shape of the pouch 2 which forms the main pouch.

In this embodiment, the pouch 20 is preferably filled with a gas, e.g. air, while the first pouch 2 is filled with a liquid, e.g. physiological water. Since the second pouch 20 is advantageously disposed to be substantially concentric with the first pouch 2, and thus to be surrounded over substantially its entire outside surface by the liquid in the pouch 2, good sealing is obtained for the pouch 20, thereby reducing the risks of the gas contained therein leaking out.

In the preferred variant embodiments shown in FIGS. 1 to 6, the first and second connection means 3 and 3' are substantially in alignment so that their respective orifices 4 and 4' can easily receive a common connection member 6. The purpose of this disposition is to greatly facilitate the difficult and essential operation of inflating and expanding the two pouches 2 and 20, by reducing the number of manipulation operations needed and also the number of instruments that are required.

In the preferred variant constituted by a two-pouch balloon 1, spacing between the pouches 2 and 20 is maintained by spacer means 10 serving to hold the two pouches 2 and 20 respectively and at a distance apart from each other.

In a preferred variant of the invention, the spacer means 10 are formed by spacers that hold and secure the two pouches 2, 20 at a distance apart from each other.

Advantageously, the intra-gastric balloon 1 in accordance with the invention has two spacers 10 that are substantially diametrically opposite from each other about the common center of the two pouches (FIG. 2).

In a variant, it is naturally possible to envisage some greater number of spacer means, without that going beyond the ambit of the invention. In particular, it is possible to envisage a series of four or even six spacers (or equivalent means) angularly spaced apart between the two pouches 2 and 20, optionally in regular manner.

Advantageously, the spacers 10 are formed by at least one, and preferably two, base plates 11 interconnected by a leg 12 forming the spacer proper, each base plate 11 being secured to the wall of a respective pouch 2, 20, e.g. by adhesive.

In the preferred variant shown in FIGS. 1 to 3, the first and second connection means 3 and 3' are common to both pouches 2 and 20, being formed by one of the spacers 10 which thus forms common connection means 10A. This disposition greatly simplifies fabrication and assembly of the intra-gastric balloon 1, while still ensuring that it is robust.

Figure 6:
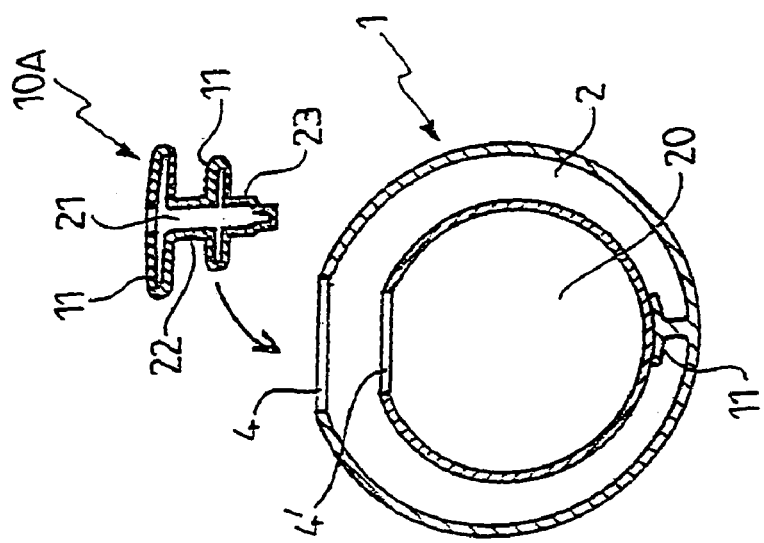
FIGS. 4, 5, and 6 are diagrammatic cross-section views showing the main steps in the method of fabricating a two-pouch intra-gastric balloon in accordance with the invention.

The spacer 10 forming the common connection means 10A is shown in detail in FIG. 3 and also in FIG. 6.

The common connection means 10A comprises a hollow central duct 21 forming the leg of the spacer, said duct 21 having two holes 22 and 23, each provided at a respective height suitable for looking into the inside volume of the first or the second pouch 2 or 20, each being associated with a respective valve 5, 5', said duct 21 being suitable for receiving the connection member 6 that is to fill each of the pouches 2, 20 differently, using a distinct filler fluid.

In known manner, the common connection means 10A is made of an elastomer material that is relatively soft, and thus not very hard, so that the holes 22 and 23 are made merely as incisions at two different levels. Because of the low hardness of the elastomer material, the valves 5 and 5' are in fact constituted by the hole or incision 22, 23 which suffices to seal each pouch merely by its own elasticity once the pouch has been filled.

As shown in particular in FIG. 1, the intra-gastric balloon in accordance with the invention may have an outside wall 2A that is made up of facets or cells that are distributed in optionally regular manner over the entire surface of the balloon 1.

This design feature, which can be totally independent of the presence or absence of one or more pouches in the intra-gastric balloon 1 in accordance with the invention, serves in particular to increase the probability of peripheral zones of contact with the stomach walls of the patient. This therefore increases the possibility and the probability of impeding the passage of food on a durable basis, thereby also tending to prolong the sensation of being sated.

The cellular shape can be obtained using a series of touching cells over the entire surface of the main pouch 2, or on the contrary by using a series of non-touching cells, with the surface between cells corresponding to a portion of a sphere, for example.

The invention also seeks to protect in individual manner the connection member 6 for providing the interface between the intra-gastric balloon 1 in accordance with the invention and one or more sources of fluid (not shown in the figures) supplying the fluid needed for implanting and expanding said balloon.

For this purpose, the invention also provides a surgical device for treating obesity, the device serving to expand a multiple-pouch intra-gastric balloon, in particular a two-pouch balloon, of the kind shown in FIG. 2.

In this configuration, the surgical device in accordance with the invention comprises a tubular connection member 6 suitable for being inserted in the hollow central duct 21 of the common connection means 10A of the intra-gastric balloon, said member 6 being provided with two independent channels 15 and 16 opening out towards one end in register with respective ones of the two holes 22 and 23 of the hollow central duct 21, said channels 15 and 16 being connected at their opposite ends to two mutually independent endpieces 17 and 18 suitable for being connected separately to respective sources of distinct filler fluids.

In the preferred variant embodiment shown in FIG. 3, the independent channels 15 and 16 are concentric. In a variant, they could nevertheless be non-concentric and separate, extending parallel to each other and spaced apart from each other inside the tubular connection member 6.

In use, it is possible to begin the operation of inflating and expanding the pouches 2 and 20, once the intra-gastric balloon 1 has been implanted in its deflated shape within the stomach of the patient via the esophagus, e.g. using an endoscope, with the tubular connection member 6 being inserted in the central duct 21, either before or after implantation.

Initially, each endpiece 17, 18 is connected and coupled to a distinct source of filler fluid, e.g. for example the endpiece 17 to a source of liquid (physiological liquid), and the endpiece 18 to a source of gas (e.g. air). The two pouches 2 and 20 can then be expanded simultaneously, e.g. using syringes, with the pressure of each fluid being sufficient to deform the incisions that constitute the holes 22, 23.

Once the required predetermined volume of fluid has been reached, the admission flow of each fluid is interrupted, and given the elasticity of the material constituting the common connection means 10A, this enables each hole 22, 23 to return to is initially closed position corresponding to a sealed position. There is thus no risk of leakage or mixing of the fluids in each of the pouches 2, 20.

The tubular connection member 6 is subsequently extracted from the hollow central duct 21, and thus from the intra-gastric balloon 1, merely by applying longitudinal or axial traction.

The intra-gastric balloon 1 in accordance with the invention can be obtained using any conventional known fabrication method that involves steps of dipping a substantially spherical mold in a bath of elastomer material, e.g. a material based on a mixture of silicone and xylene.

Figure 4:
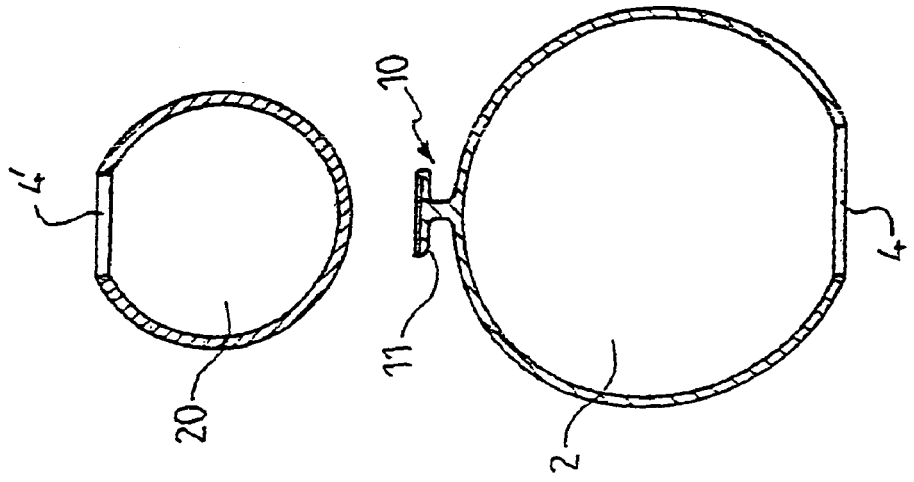

Nevertheless, the intra-gastric balloon in accordance with the invention is advantageously obtained by means of a method of injecting silicone-based elastomer materials into molds so that, during an initial injection step, each of the two pouches 2, 20 is obtained separately and includes its respective orifice 4, 4', as shown in FIG. 4.

During this first step, the fabrication method of the invention is thus a method in which the first and second pouches are fabricated by injecting an elastomer material into a mold so as to obtain two pouches, each having a respective orifice 4, 4', the first pouch being of dimensions greater than those of the second pouch, so that said second pouch can be inserted inside the first pouch with sufficient peripheral distance between them.

Thereafter, during the step of injecting the elastomer material of the first pouch, or subsequently, the method of manufacture consists in a subsequent step in putting a spacer 10 into place on the outside face of the first pouch, substantially opposite from its orifice 4, the spacer 10 presenting a free external base plate 11 facing towards the outside of said first pouch.

The spacer 10 can be put into place directly during the step of fabrication by injecting elastomer, the spacer 10 then being made directly, likewise by injecting elastomer.

In a preferred variant, the spacer 10 can be made independently during a distinct injection step using a different elastomer material. In which case, the spacer 10 is secured to the outside face of the pouch 2 by adhesive, at a position that is substantially opposite from and in register with the orifice 4.

Figure 5:
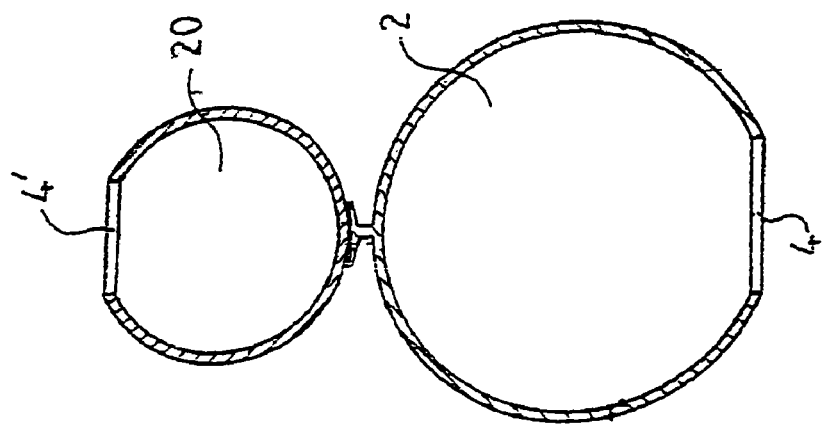

Thereafter, as shown in FIG. 5, the two pouches 2 and 20 are stuck to each other via the free outside base plate 11 at the outside face of the second pouch 20, at a location which is situated substantially opposite from or in register with the corresponding orifice 4'.

Thereafter, the first pouch 2 is turned inside out so as to cause the second pouch 20 to penetrate therein through the orifice 4, thereby obtaining a disposition of the kind shown in FIG. 6 where the second pouch 20 is situated inside the pouch 2 and is substantially concentric therewith, the two orifices 4 and 4' being in axial alignment and in register with each other.

In an additional step, the common connection means 10A is put into place, said means being fabricated separately during a separate step of injection-molding an elastomer material.

In this additional step, the common connection means 10A for the two pouches is put into place via the two substantially-aligned orifices 4 and 4' of the first and second pouches 2 and 20, and then said common means 10A is bonded with adhesive via its two anchor base plates or feet 11 to each of the annular portions surrounding the orifices 4 and 4'.

The method of fabrication by injecting elastomer material is thus found to be simple and quick to implement, thereby reducing industrial constraints.

In totally independent manner, the invention also provides an intra-gastric balloon for treating obesity, the balloon being for implanting in the stomach of a patient in order to reduce the volume of the stomach, said balloon comprising an outside wall for coming into contact with the stomach wall, the balloon subdividing the stomach into an upstream zone and a downstream zone so as to constitute a barrier to the passage of food between said two zones, the outside wall being shaped in such a manner as to co-operate with the stomach wall to define channels for passing food from the upstream zone towards the downstream zone.

It appears that although the main factor influencing weight loss in a patient, while the patient is being treated by means of an intra-gastric balloon, is constituted by the volume that the balloon occupies in the patient's stomach, other factors also need to be taken into consideration. Thus, the way in which the balloon makes contact with the stomach walls, whether in terms of balloon texture or in terms of the shape of the contact area between the balloon and the stomach wall, can play an important role in the effectiveness of the treatment by a intra-gastric balloon, or at least in the comfort of such treatment.

It is found that a portion of the surface of the balloon, which corresponds generally substantially to a circumferential band, becomes pressed against the gastric wall when the balloon is in place in the stomach. The balloon thus forms a barrier between an upstream zone of the stomach which is in communication with the esophagus, and a downstream zone of the stomach which is in communication with the remainder of the digestive tract. When the peripheral band of contact between the balloon and the stomach wall is wide, which corresponds to a large contact interface between the balloon and the stomach wall, then the balloon constitutes an extremely effective barrier for food coming from the upstream zone and that is to pass into the downstream zone in order subsequently to reach the remainder of the digestive tract. This occurs in particular when the balloon used is spherical with a surface that is smooth, or at least regular. Under such circumstances, a perimetric band of greater or lesser width on the outside surface of the balloon fits closely to the stomach walls, thereby preventing food from the esophagus from going past and thus being digested. When a large quantity of food has accumulated in the upstream zone, that leads to a mechanical load on the balloon which leads to localized areas of the balloon wall separating from the stomach wall, thus allowing the food to go past.

The balloon thus acts as a plug, thereby greatly disturbing the digestion of food and can lead to acidity of the stomach (heartburn) that is particularly uncomfortable for the patient.

In order to overcome this difficulty, proposals have been made, as described in U.S. Pat. No. 4,694,827, for an intra-gastric balloon whose outside surface is provided with lobes, which are supposed to perform two functions: specifically those of defining channels between the surface of the balloon and the wall of the stomach while minimizing contact area between the stomach wall and the balloon.

Although such a design is effective in achieving substantially tangential contact between the envelope of the balloon and the wall of the stomach, thereby reducing the risk of the balloon inflicting trauma on the gastric wall, it nevertheless allows food to pass extremely easily and quickly to the remainder of the digestive tract, and thus does not procure a prolonged sensation of being sated for the patient.

Unfortunately, part of the reason why the treatment is effective lies in the barrier effect provided by the balloon, i.e. in the difficulty that is encountered by food in passing from the upstream zone towards the downstream zone of the stomach, thereby prolonging the patient's feeling of being sated.

Consequently, the invention seeks to remedy the above-mentioned drawbacks and to provide a novel intra-gastric balloon of a shape that enables contact between the balloon and the stomach wall to be minimized so as to guarantee passage of food from the upstream zone towards the downwards zone, while nevertheless ensuring that the time taken for such passage is sufficiently long to optimize the stated sensation that the balloon induces.

Another object of the invention seeks to propose a novel intra-gastric balloon presenting a non-traumatic nature.

Another object of the invention is to provide a novel intra-gastric balloon that is particularly simple and inexpensive to fabricate.

The objects given to the invention are achieved by an intra-gastric balloon for treating obesity, for implanting in the stomach of a patient in order to reduce the volume of the stomach, said balloon comprising an outside wall for coming into contact with the wall of the stomach, the balloon subdividing the stomach into an upstream zone and a downstream zone in order to constitute a barrier for the passage of food between these two zones, the outside wall being shaped so to co-operate with the wall of the stomach to define channels for passing food from the upstream zone to the downstream zone, the balloon being characterized in that the outside wall is shaped so that the channels form a network branching at more than two points, so as to constitute a path of tree structure for food passing from the upstream zone to the downstream zone.

Figure 7:
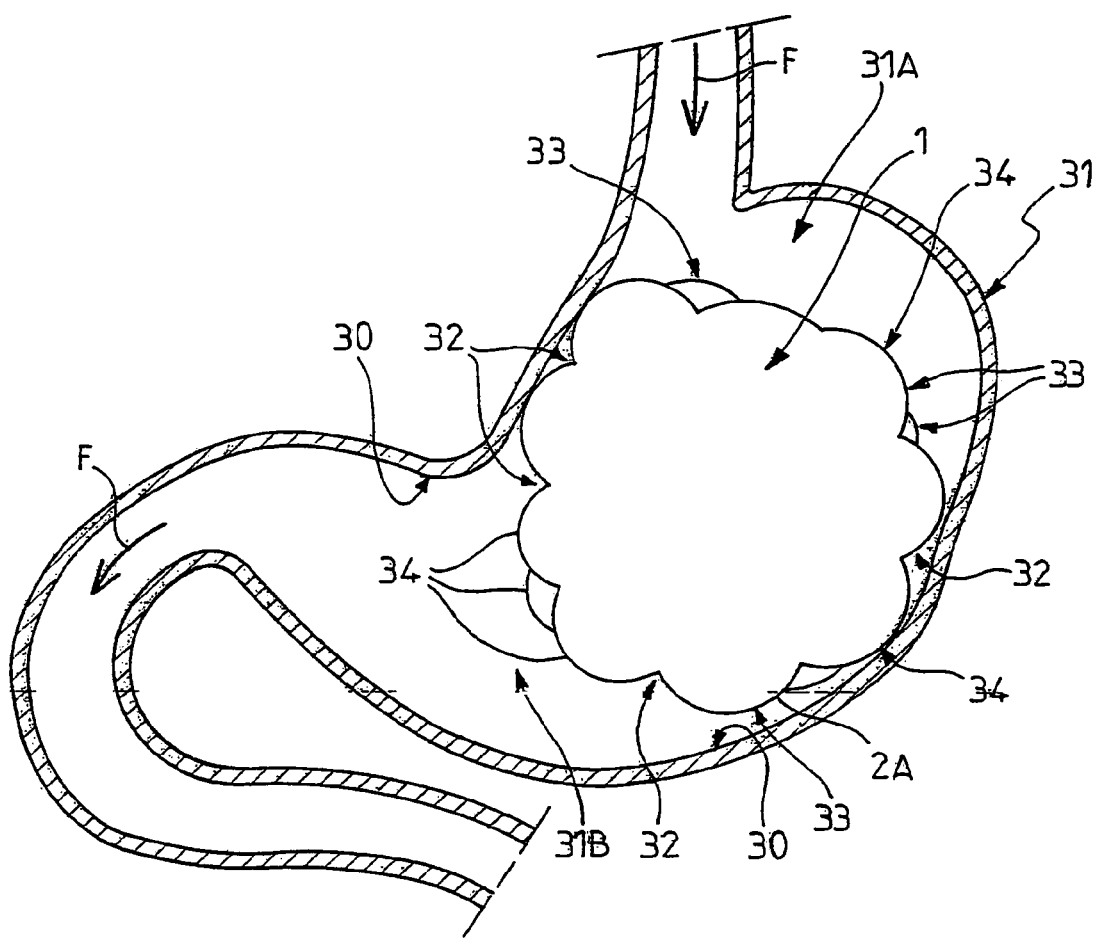
FIGS. 7 to 10 show variant intra-gastric balloons in accordance with another aspect of the invention.
Figure 8:
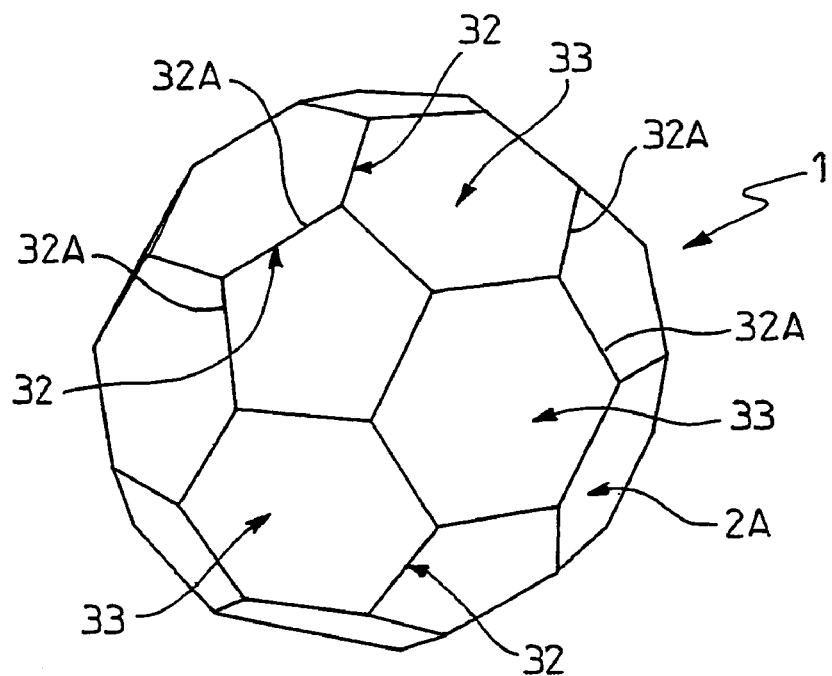
Figure 9:
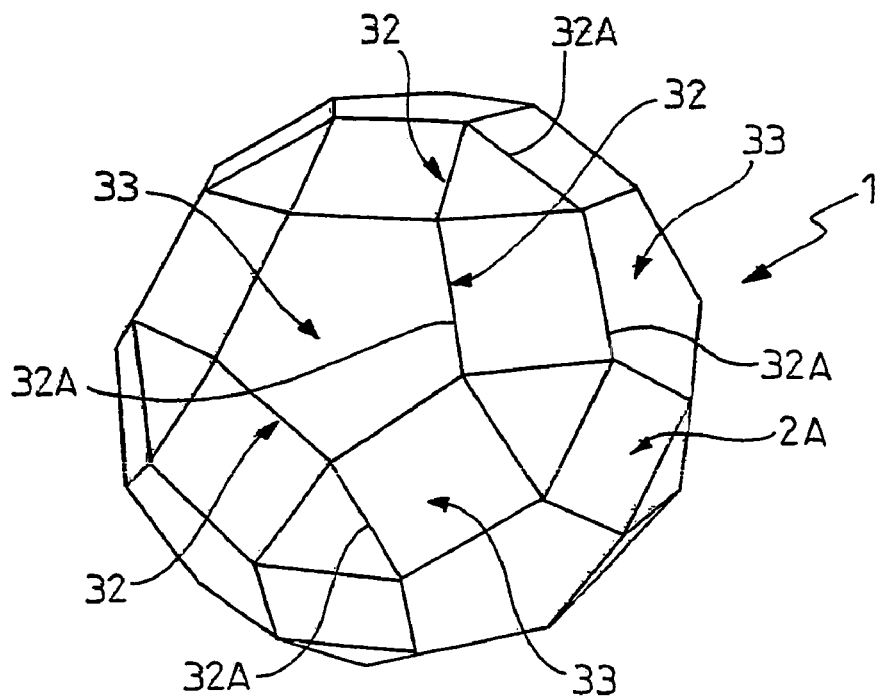
Figure 10:
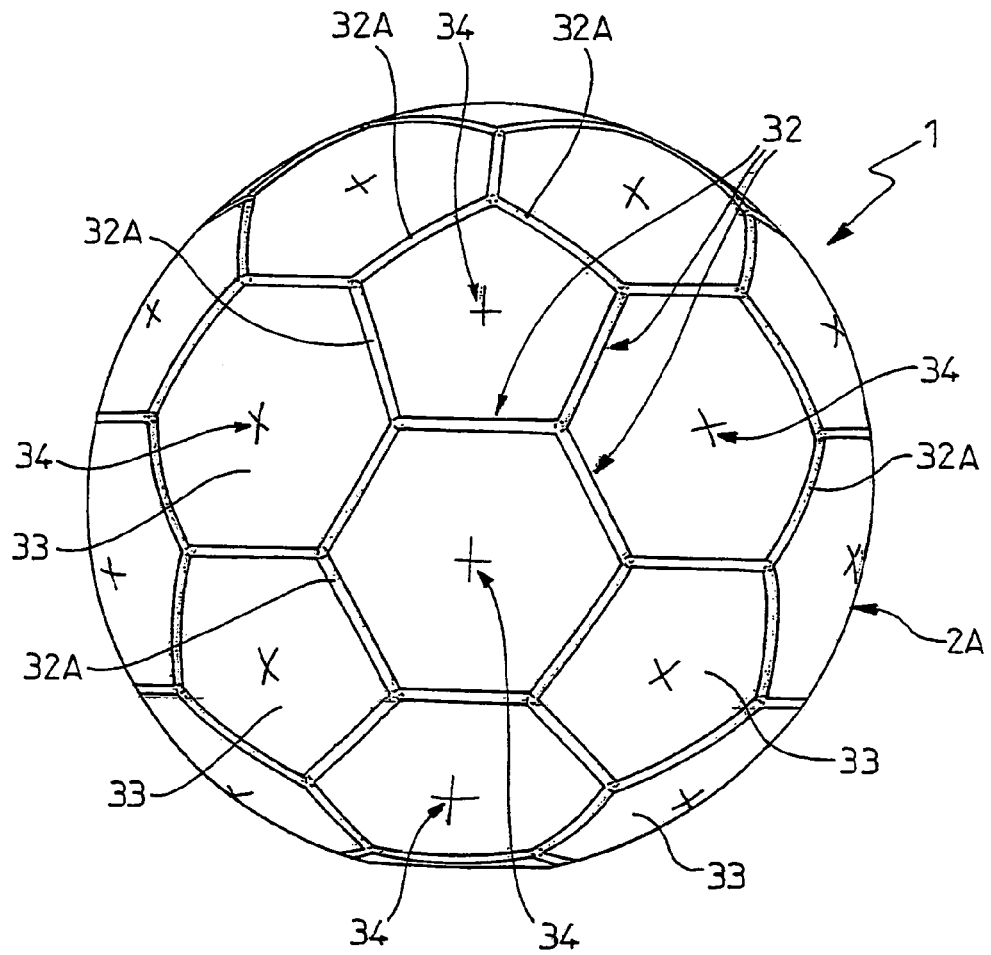

Other objects and advantages of the invention will appear better on reading the following detailed description and also with the help of the accompanying drawings, given purely by way of non-limiting illustration, and in which:

FIG. 1 is a perspective view of an intra-gastric balloon in accordance with the invention, in a first embodiment;

FIG. 7 is a diagrammatic section view of an intra-gastric balloon in accordance with the invention pressed against the stomach wall;

FIG. 8 is a perspective view of a second embodiment of an intra-gastric balloon in a position of incomplete expansion;

FIG. 9 is a perspective view of a third embodiment of an intra-gastric balloon of the invention in a position of incomplete expansion; and FIG. 10 is a perspective view of the FIG. 8 balloon in its position of maximum expansion.

FIGS. 1 and 7 to 10 show an intra-gastric balloon 1 in accordance with the invention. Such a balloon is designed to treat obesity and is for implanting in the stomach of a patient in order to reduce the volume of the stomach, insofar as the balloon occupies a major portion of the space that would otherwise be available for food.

In the text below, reference is made to a balloon constituted by a flexible pouch that can be expanded by being filled with fluid, the pouch being constituted by an envelope made using a flexible material, e.g. an elastomer, and having an outside face in the form of an outside wall 2A that is to come into contact with the wall 30 of the stomach 31. Such an embodiment enables the balloon to occupy firstly a folded or slack configuration (not shown in the figures) in which it occupies a small volume, thereby making it easier to implant, and secondly, by using one or more inflation fluids (e.g. a liquid and/or a gas), an expanded configuration of predetermined volume, e.g. about 600 mL, corresponding to its volume in use, as shown in particular in FIGS. 1, 7, and 10. Between the folded configuration and the expanded configuration, the balloon 1 passes through intermediate inflation configurations shown in FIGS. 8 and 9, where the balloon is close to its nominal in-use volume, but has still not quite reached it (inflation incomplete).

Nevertheless, it is entirely possible, without going beyond the ambit of the invention, for the intra-gastric balloon 1 in accordance with the invention to present a structure that does not present an expandable nature, but rather a nature that is rigid or semi-rigid. It is also possible, without going beyond the ambit of the invention, to envisage that the balloon 1 is constituted by a foldable structure which, for expansion, does not require a fluid, but relies on an elastic effect or on implementing shape-memory structures.

The balloon 1 of the invention thus occupies sufficient volume within the stomach for it to be capable of pressing against the wall 30 of the stomach 31.

In this way, the balloon 1 subdivides the stomach 31 into an upstream zone 31A and a downstream zone 31B. The upstream zone 31A is thus situated upstream from the balloon 1 in the digestive flow direction F of food ingested by the patient, while the downstream zone 31B is downstream from said balloon, in the digestive flow direction F of the food. The zone 31A thus communicates with the esophagus, while the zone 31B is in communication with the remainder of the digestive tract, i.e. with the intestines.

The balloon 1 thus constitutes a barrier to food passing from the upstream zone 31A towards the downstream zone 31B.

Optimizing the effectiveness of the balloon lies not only in the volume it occupies in the stomach, and that therefore limits the space available for food, but also in controlling the extent to which food manages to pass the barrier constituted by the balloon 1.

For this purpose, in accordance with the invention, the outside wall 2A of the balloon 1 is shaped to co-operate with the wall of the stomach 30 to define channels 32 for passing food from the upstream zone 31A towards the downstream zone 31B.

These channels 32 provide a function of allowing solid and/or liquid food to go from the upstream zone 31A to the downstream zone 31B by going past the barrier constituted by the balloon 1.

In accordance with an essential characteristic of the invention, the outside wall 2A is shaped so that the channels 32 are interconnected in such a manner as to form a network that branches at more than two points, thereby constituting a tree-structure path for food passing from the upstream zone 31A to the downstream zone 31B.

The term "network branching at more than two points" is used herein to mean that channel junctions or subdivisions are provided at at least three points in the network of channels.

The general concept of the invention thus seeks firstly substantially to guarantee that food can pass from the upstream zone 31A to the downstream zone 31B via the channels 32, thus making it possible to avoid the drawbacks associated with a "plug" effect that the balloon can produce if it comes into substantially leaktight contact with the wall 30 of the stomach 31. In addition, while ensuring that food can indeed pass, the intra-gastric balloon 1 in accordance with the invention nevertheless generates a path that is tortuous, with multiple subdivisions to be followed by food between the walls of the stomach and of the balloon, because of the network being formed with more than two branching points for the channels 32. Food is thus guaranteed to pass substantially continuously from the upstream zone 31A to the downstream zone 31B, but at a rate that is slow, as imparted by the branching, i.e. subdivided, nature of the network of food-passing channels 32 between the stomach wall 30 and the outside wall 2A of the balloon 1. Such an arrangement enables the total length of time for digesting food to be increased, thus prolonging the sensation of being sated, while nevertheless significantly eliminating any "plug" effect.

Below, reference is made to a balloon that is substantially round in shape, or that can at least be inscribed in a sphere. Nevertheless, such a configuration is given purely by way of example, and the general shape of the balloon 1 in accordance with the invention could thus optionally be close to that of an ellipsoid, or indeed of an ovoid, for example.

Advantageously, the intra-gastric balloon 1 of the invention has a plurality of projections 33 disposed relative to one another in such a manner that the food-passing channels 32 going from the upstream zone 31A to the downstream zone 31B are defined firstly by the spaces or gaps between the projections 33, and secondly by the stomach wall 30 coming into contact with the tops 34 of said projections 33.

The term "projection" is used herein to mean a protuberance or extension of substantially rounded or regular convex shape. Each projection 33 presents a top 34 that is to come into contact with the gastric wall 30. Contact between said wall 30 of the stomach 31 and the balloon 1 thus takes place at a plurality of substantially tangential contact points, thereby minimizing the total area of contact between the gastric wall 30 and the balloon 1, and thus considerably reducing the risk of trauma. The projections 33 are arranged to be sufficiently close to one another so that their bases define grooves or passages which are closed by the wall 30 of the stomach 31 so as to form channels 32 for conveying and guiding liquid or solid food from the upstream zone 31A to the downstream zone 31B.

The projections 33 are also disposed in such a manner that each passage is subdivided into two or more branches, at more than two points. This subdivision or branching effect creates a tree-structure path for food which contributes to increasing the time taken by food to travel from the upstream zone 31A to the downstream zone 31B as compared with a direct path of the kind described in U.S. Pat. No. 4,694,827.

Advantageously, and as shown in FIGS. 8 to 10, each projection 33 projects from a base that is substantially polygonal in shape. Preferably, the substantially polygonal bases touch one another via their sides 32A, at least over a portion, and preferably over all, of the surface of the outside wall 2A.

The outside wall 2A of the balloon may thus present a multitude of facets or cells that are separated in optionally regular manner over all or part of its surface, each facet forming the base of a projection 33 whose top 34 is substantially in register with the center of the facet. The facets may be strictly plane, or they may be curved or bulging to a greater or lesser extent, particularly once the balloon has been fully inflated, as shown in FIGS. 1 and 10.

In the embodiments shown in FIGS. 8 to 10, the polygonal bases from which the projections 33 extend may be of different kinds and present different shapes and/or differing numbers of sides.

Preferably, the bases are arranged relative to one another substantially in a polyhedral pattern that is regular or semi-regular.

It can thus be envisaged that the polygonal spaces are arranged in the pattern of a dodecahedron or an icosahedron.

Preferably, the bases are arranged in a semi-regular polyhedral pattern (an Archimedian polyhedron) such as a truncated dodecahedron, a truncated icosahedron (as shown in FIGS. 8 to 10), an isocadodecahedron, a minor rhombocuboctahedron, a major rhombocuboctahedron, a minor rhomboicosidodecahedron (shown in FIG. 9), or indeed a' major rhomboicosidodecahedron, said list not being limiting in any way.

In preferred manner, the envelope of the balloon is formed by assembling together polygonal bases via their sides 32A, with the core 33 of each base as defined by its sides 32A presenting flexibility or deformability that is greater than that of said sides 32A, such that during inflation of the pouch formed by the envelope by being filled with fluid, the core 33 of each base deforms to a greater extent than do the edges forming the sides 32A of each base, thereby generating the protuberances that form the projections 33, with the tops 34 of these protuberances being situated substantially vertically over the center of the polygon formed by the sides 32A of each base.

Each base thus forms a facet from which a projection 33 is generated.

It is thus possible to envisage making the envelope out of an elastomer material so that the core 33 of each base or facet is of thickness that is smaller than that of the sides 32A of each base or facet, thereby achieving a difference of flexibility between the core 33 and the sides 32A of each base or facet. Thus, under the effect of mechanical force, specifically, internal inflation pressure, the zones of greater thickness, i.e. the sides 32A, deform little or not at all, whereas the zones of smaller thickness, i.e. the core of each facet 33, deform to a greater extent so as to form the projections 33, thus enabling a bulging or bumpy surface to be obtained for the outside wall 2A, i.e. a surface formed by alternating convex or concave surfaces, with a branching network of passages being created as a result between the projections 33.

Alternatively, it is possible to envisage making the envelope of a balloon in accordance with the invention by associating a fabric, i.e. a woven textile or merely a grid or trellis, with an elastomer film forming the core of each base or facet, the mesh made of said fabric forming the sides of the bases from which the projections 33 extend and being less deformable than the elastomer film, so as to create a projection 33 in the middle of each mesh. The fabric and the elastomer film may be associated with each other by embedding the reinforcing fabrics, for example, in an elastomer matrix, e.g. made of silicone. During inflation of the envelope, the textile acts as reinforcement so that only the elastomer material in the core of each facet-forming mesh deforms.

In another variation embodiment (not shown), it is entirely possible to envisage that the outside wall 2A presents a shape that is substantially smooth and spherical, having projections scattered thereover in the form of spherical caps, said projections being distributed over the entire surface of the outside wall 2A and sufficiently close to one another to define passages that co-operate with the wall 30 of the stomach to contribute to forming channels 32 in accordance with the invention.

Thus, when the balloon 1 in accordance with the invention is in position in the stomach, being prevented from moving laterally and peripherally against the wall of the stomach, food present in the upstream zone 31A can follow a first channel 32, and then encounter a first obstacle formed by a projection 33 which subdivides the channel 32 into at least two channels, and so on. This arrangement allows food to pass in calibrated and controlled manner towards the reminder of the digestive circuit.

In a manner that is completely independent of the technical characteristics described above, the invention also provides an intra-gastric balloon for treating obesity that is to be implanted in the stomach of a patient to reduce the volume of the stomach, said balloon comprising a flexible envelope defining a predetermined inside volume, said flexible envelope being made of an elastomer material.

The invention also relates in independent manner to a method of manufacturing an intra-gastric balloon for treating obesity, said balloon for being implanting in the stomach of a patient in order to reduce the volume of the stomach.

Intra-gastric balloons implemented in the form of a single-piece pouch of expandable silicone, generally of spherical shape, are well known. They are generally made by dipping. The dipping process consists in dipping a core having the shape desired for the balloon (e.g. a sphere, an ovoid, or an ellipsoid) in a bath of silicone dispersed in a solvent, in causing the film that is formed on the surface of the core by such dipping to dry, and then in unmolding the core.

Although such a method of manufacture generally gives satisfaction, it nevertheless presents numerous drawbacks.

Because of the presence of a solvent that is inflammable and toxic in the dipping bath, it is necessary to use special equipment, both for the machinery and for the premises (an explosion-proof room) in order to guarantee health and safety for personnel. In addition, the method is particularly difficult to implement since it requires accurate control of the fluidity of the dipping bath, which requires constant monitoring and topping up with solvent, the solvent generally being very volatile.

That method thus requires staff to be particularly highly qualified.

In addition, it is generally necessary to proceed with a plurality of dipping steps in order, by iteration, to obtain the desired final thickness for the envelope. Between successive dipping steps, care must be taken to ensure that the solvent evaporates so as to enable the layer of material that has been deposited on the core to cure (cross-link). Under such circumstances, the method of manufacture by dipping turns out to be particularly lengthy since it requires sequences of operations of different kinds (dipping, displacement, passing through an oven to evaporate off the solvent, etc.), requiring the use of a conveyor carousel, which means that the cycle time for obtaining a balloon is of the order of half a day. In addition, the fact of making the balloon as a stack of distinct successive layers leads to a risk of incomplete cohesion between two adjacent layers, and that can be harmful for the unitary nature desired for the balloon.

Furthermore, the dipping method generally does not enable the thickness of the balloon envelope to be controlled accurately. Although balloons obtained by dipping generally give satisfaction, they nevertheless provide insufficient dimensional accuracy, which can lead to certain zones of the balloon being too thick, thereby increasing the cost of producing the balloon, or to certain other zones of the balloon not being thick enough, which can lead to the balloon being fragile.

Finally, the field of application of the method is further restricted by the fact that it does not make it possible to achieve controlled variations in thickness and/or shape over a single piece. As a result, the design of an intra-gastric balloon that is to be fabricated using this method remains tied to causing a fluid to flow over a core, thereby considerably reducing the options for associating shapes and dimensions in a single part, which amounts to limiting the functions that it can perform.

Consequently, the objects given to the invention seek to remedy the various drawbacks listed above and to propose a novel intra-gastric balloon that presents improved regularity and strength.

Another object of the invention is to propose a novel method of fabricating an intra-gastric balloon that enables balloons to be fabricated in a manner that is more reliable, and simpler, for lower cost.

Another object of the invention seeks to propose a novel method of fabricating an intra-gastric balloon that enables balloons to be fabricated quickly and with excellent dimensional regularity.

Another object of the invention seeks to propose a novel method of fabricating an intra-gastric balloon using a small number of steps.

The objects given to the invention are achieved by means of an intra-gastric balloon for treating obesity, for implanting in the stomach of a patient to reduce the volume of the stomach, said balloon comprising a flexible envelope defining a predetermined inside volume, said flexible envelope being made of an elastomer material, the balloon being characterized in that the dimensional tolerance on the nominal thickness of the envelope lies in the range 1% to 20%.

The objects given to the invention are also achieved by means of a method of fabricating an intra-gastric balloon for treating obesity, said balloon being for implanting in the stomach of a patient in order to reduce the volume of the stomach, the method being characterized in that it includes an injection step in which an elastomer material is injected into a mold in order to obtain a flexible pouch that is to from the envelope on the balloon.

Figure 11:
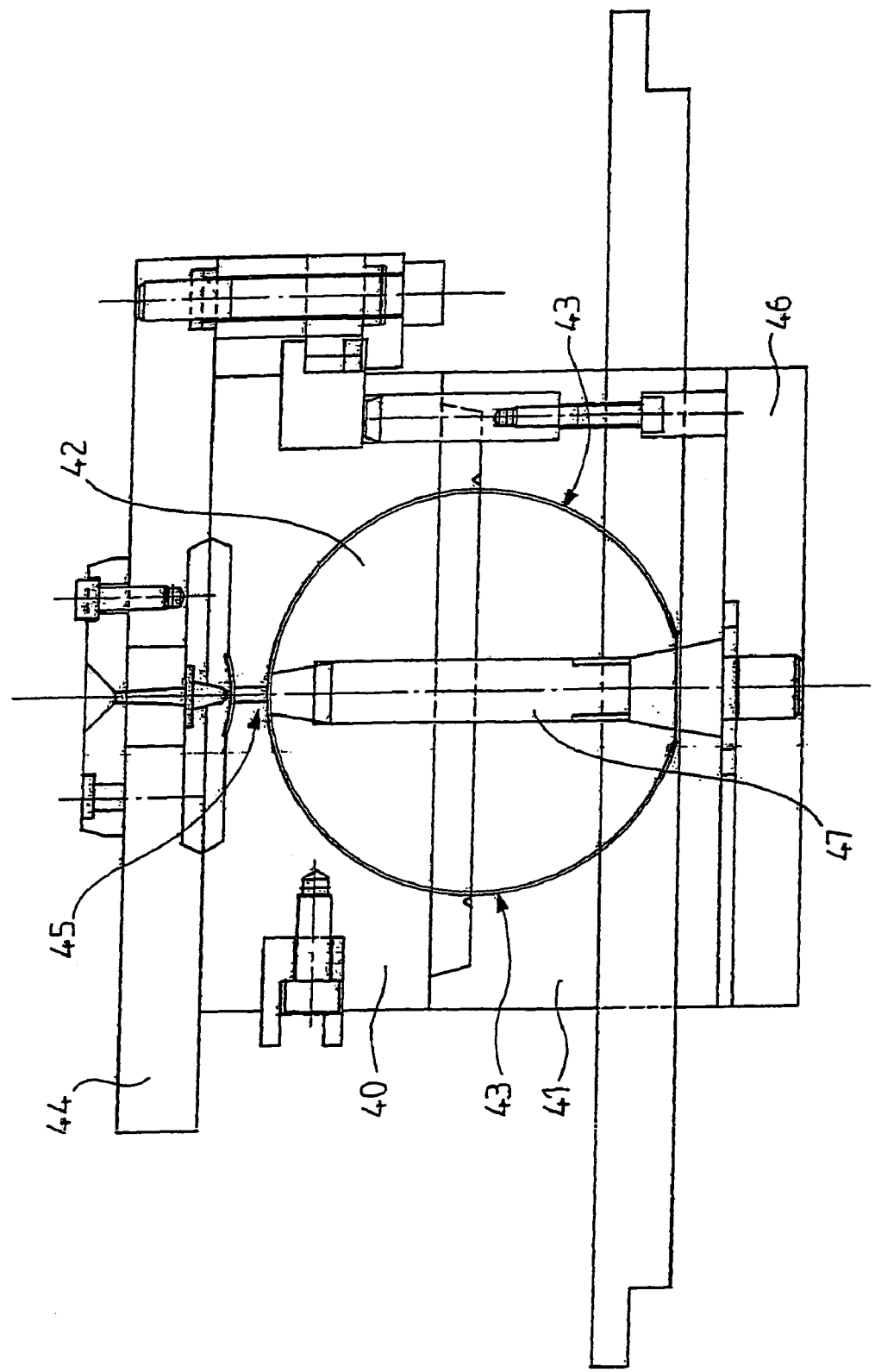
FIGS. 11 and 12 show means for fabricating intra-gastric balloons in accordance with another aspect of the invention.
Figure 12:
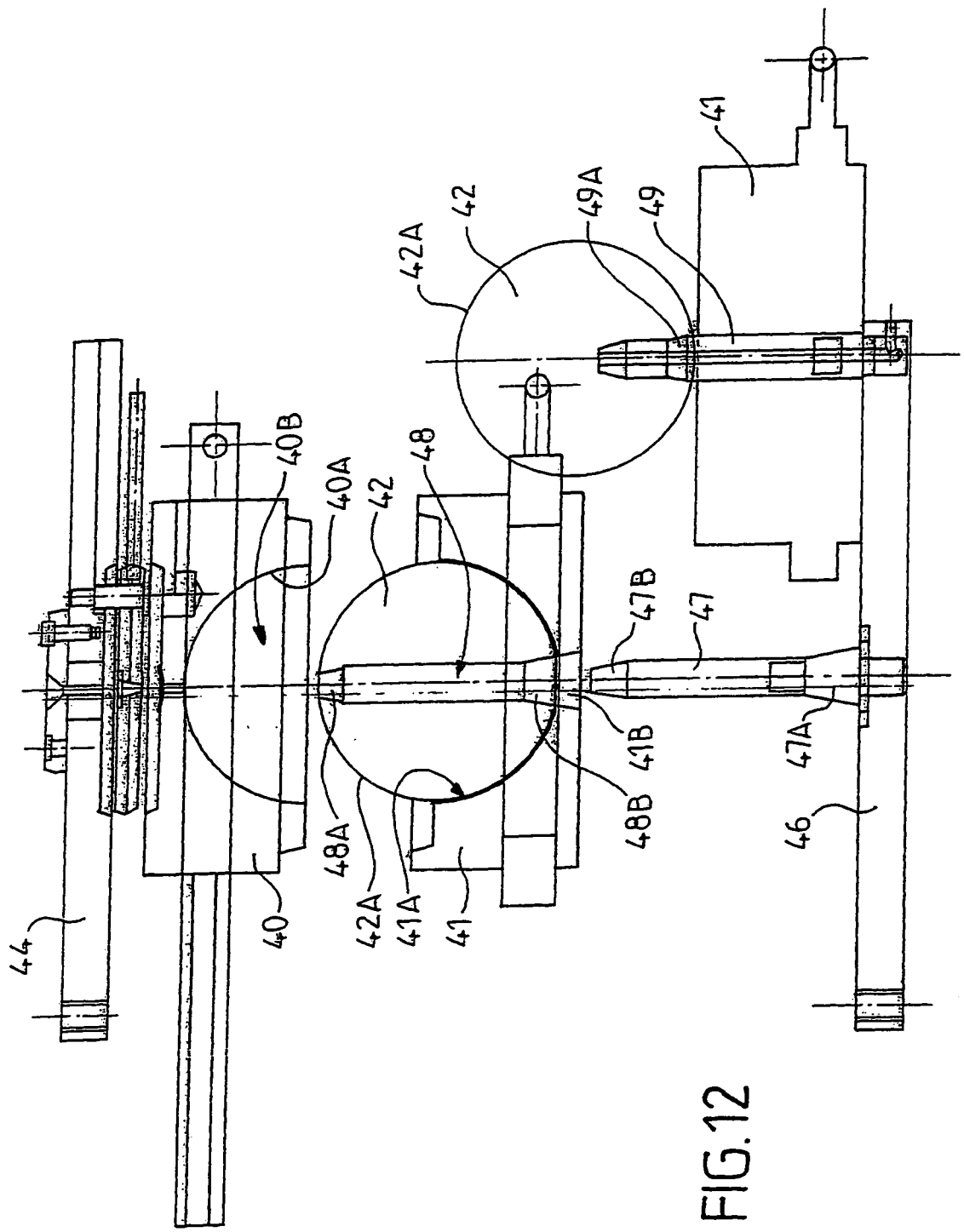

Other objects and advantages of the invention will appear better on reading the following description and from the accompanying drawings given purely by way of non-limiting illustration, and in which:

FIG. 1 is a perspective view of an intra-gastric balloon in accordance with the invention;

FIG. 10 is a perspective view of a balloon in accordance with the invention constituting a second embodiment;

FIG. 11 is a side view of a mold in the closed position that enables the method in accordance with the invention to be implemented; and FIG. 12 is a side view showing the FIG. 11 mold in the open position, i.e. in the unmolding position.

The invention relates to an intra-gastric balloon 1 for treating obesity, the balloon being for implanting in the stomach of a patient so as to reduce the volume of the stomach. Such a balloon 1 generally comprises at least one flexible envelope 2 defining a predetermined inside volume, said flexible envelope 2 being made of an elastomer material, e.g. based on silicone.

The flexible envelope 2 thus forms a pouch that is expandable, enabling it to occupy firstly a folded or slack configuration (not shown), in which it occupies a small volume that facilitates implantation, and secondly, by using an inflation fluid, an expanded configuration of predetermined volume (shown in FIGS. 1 and 10), e.g. of about 600 mL, corresponding to its volume when in use in the stomach.

The flexible envelope 2 of the intra-gastric balloon 1 in accordance with the invention constitutes a single piece.

In the description below, reference is made to an envelope which is spherical, it being understood that the invention is not restricted to this single shape and can be applied to any type of shape, for example ellipsoid or ovoid shapes, without thereby going beyond the ambit of the invention. The envelope 2 of the intra-gastric balloon 1 may be in the form of a uniform membrane of substantially smooth or regular shape, or it may be in the form of a membrane that presents projections or lobes, as shown in FIGS. 1 and 10.

According to an essential characteristic of the invention, the dimensional tolerance T for the nominal thickness $e_{nom}$ of the envelope 2 of the intra-gastric balloon 1 in accordance with the invention lies in the range 1% to 20%, i.e. the real thickness e of the envelope can lie in the range $e_{nom}(1-T)$ to $e_{nom}(1+T)$.

For example, if the dimensional tolerance T is 10%, i.e. 0.1, then the real thickness e may vary, for a given envelope, over the range $e_{nom}(1-0.1)$ to $e_{nom}(1+0.1)$, i.e. 0.99 $e_{nom}$ to 1.1 $e_{nom}$.

In order to verify whether a given envelope does indeed satisfy the above-mentioned criterion for dimensional tolerance, it is possible to use any metrology method commonly implemented in industry.

Purely by way of illustration, and in absolutely non-limiting manner, a method implementing the following steps could be adopted:

calculating the difference E using the following equation:

$$E=100(e_{max}-e_{nom})/e_{nom} \text{ if } |e_{max}-e_{nom}|\geq|e_{min}-e_{nom}|$$

or $$E=100(e_{nom}-e_{min})/e_{nom} \text{ if } |e_{max}-e_{nom}|\leq|e_{min}-e_{nom}|$$

where $e_{nom}$ may be taken to be the arithmetic mean of the envelope thicknesses measured at a meaningful number N of measurement points distributed over the envelope, $e_{min}$ being the smallest measured thickness amongst the N points and $e_{max}$ being the greatest measured thickness amongst the N points, comparing E with T:
if $E \leq T$, then the balloon that is being inspected is in accordance with the invention.

Thickness may be measured, for example, using a mechanical thickness comparator, for example the Mitutoya NO7304 mechanical comparator. By way of example, for a balloon 1 that is substantially spherical in shape or that can be inscribed substantially in a sphere, the number of measurement points N may be equal to sixteen, with the measurement points being distributed as follows:

the substantially spherical envelope 2 is notionally subdivided by means of four meridians that are regularly spaced apart angularly;
measurements are taken at four points on each meridian, e.g. at two points close respectively to each of the poles of the spherical envelope, and at two points close to the equator of the substantially spherical envelope, e.g. distributed on either side of said equator.

The set of N measurement points must naturally be selected in such a manner as to ensure that all of the points correspond to material of the same category. Thus, if the balloon under consideration is a balloon having lobes or facets, such as the balloons shown in FIGS. 1 and 10, then all endpoints must either be selected so as to be positioned in facet cores 33, or else they must be selected so they are all positioned on the edges 32A forming the sides of the facets. With such a balloon, the edges forming the sides 32A of each facet are generally thicker than the core 33 of each facet, so as to form a balloon surface that bulges when the balloon is inflated. Similarly, care should be taken to ensure as a general rule that none of the measurement points is positioned on a singularity of the balloon, where such a singularity is constituted by a join plane, a reinforcement (e.g. next to the valve), or by any other element.

Advantageously, the dimensional tolerance on the thickness of the balloon envelope lies in a range extending from 10% to 16%. As an example of an intra-gastric balloon in accordance with the invention, mention can be made of a balloon comprising a silicone envelope of nominal thickness substantially equal to 0.5 millimeters (mm), with tolerance lying in the range 10% to 16%. This means that the nominal thickness of the pouch is 0.5 mm whereas its real thickness can vary over the range 0.5±0.8 mm (where the tolerance T is equal to 16%) to 0.5±0.05 mm (where the tolerance T is equal to 10%).

In the above, it is assumed that the envelope 2 of the balloon is made of silicone or is based on silicone. Nevertheless, it is entirely possible to envisage said envelope being made of any other elastomer material, without thereby going beyond the ambit of the invention.

The invention also provides a method of fabricating an intra-gastric balloon 1 for treating obesity, said balloon being for implanting in the stomach of a patient in order to reduce the volume of the stomach.

According to an essential characteristic of the invention, the method of fabrication comprises an injection step in which an elastomer material of the silicone kind is injected into a mold in order to obtain a flexible pouch that is to form the envelope 2 of the balloon 1.

Advantageously the mold comprises:
a top cavity 40 comprising a concave shape 40A defining in hollow form a portion of the surface of the flexible pouch that is to be obtained; and
a bottom cavity 41 comprising a hollow shape 41B defining in hollow form surface additional to that of the top cavity 40 so that when the top and bottom cavities 40 and 41 are pressed together, a closed internal volume is obtained that is substantially leaktight and defined by a surface 40A, 41A that is of shape that corresponds to the shape of the flexible pouch that is to be obtained. The top and bottom cavities 40 and 41 can thus present shapes 40A and 41A that are generally hemispherical or hemiellipsoidal, for example. Naturally, other shapes could be envisaged, without thereby going beyond the ambit of the invention.

The mold also comprises a core 42 formed by a convex body whose outside surface is complementary to the surface of the inside volume defined by the top and bottom cavities 40 and 41, ignoring a change in scale. The outside surface of the core 42 is thus a smaller-scale version of the surface of the inside volume defined by the top and bottom cavities 40 and 41. The core 42 is for positioning inside the inside volume at uniform distance from the walls defining the inside volume. This provides the arrangement shown in FIG. 11, where the top and bottom cavities 40 and 41 enclose the core 42 so as to define a gap or interstice 43 which is an empty space defined firstly by the outside surface 42A of the core 42 and secondly by the inside surface 40A, 41A of the inside volume defined by the top cavity 40 when associated with the bottom cavity 41. When it is desired to obtain a pouch that is of substantially spherical shape and made as a single piece, corresponding to the case shown in FIGS. 11 and 12, the injection method thus includes, prior to the injection step proper, a mold preparation step in which the top and bottom cavities 40 and 41 of generally hemispherical shape are pressed one against the other so as to obtain an inside volume that is substantially spherical in shape, with a spherical core 42 being previously placed between the two cavities 40 and 41 concentrically with said inside volume, the diameter of the core being smaller than that of said inside volume defined by the top and bottom cavities 40 and 41. This step of preparing the mold is followed by an injection step in which an elastomer material, which may be silicone gum or liquid silicone, for example, is injected into the interstitial space 43 extending between the core 42 and the top and bottom cavities 40 and 41, thereby obtaining a pouch of generally spherical shape that is to form the envelope 2 of the intra-gastric balloon.

Advantageously, the top cavity 40 is secured to a top soleplate 44 so that the inside space 40B defined by the concave shape 40A of the cavity 40 is in fluid communication with the top soleplate 44, which itself carries means for injecting elastomer material, which injection means are themselves in communication with the injection press (not shown).

In preferred manner, the injection means comprise three injection nozzles angularly distributed in regular manner (i.e. spaced apart at 120° intervals) around or at the top 45 of the inside volume defined by the top and bottom cavities 40 and 41. The top 45 thus corresponds substantially to the point where the concave shape 40A of the top cavity 40 comes closest to the top soleplate 44.

The injection nozzles preferably all inject at identical rates.

Advantageously, the method also makes use of a bottom soleplate 46 on which there is fixed a pin 47 for centering the core 42. As shown in FIGS. 11 and 12, the core 42 can be in the form of a solid sphere, for example, having a bore 48 of shape complementary to that of the centering pin 47 so as to enable the core 42 to be engaged in fitted manner on the pin 47 inside the bottom cavity 41, which includes for this purpose a through opening 41B for passing the centering pin 47.

The bore 48 and the centering pin 47 are designed so as to minimize any risk of seizing between the core 42 and the centering pin 47. For this purpose, the steels constituting the core 42 and the centering pin 47 should preferably present different hardnesses, e.g. 49 HRc or 50 HRc for the centering pin 47 and 35 HRc for the core 42 (hardness on the Rockwell scale). It is also possible for the centering pin 47 to be provided with a base 47A of generally frustoconical shape, and with an opposite end 47B also of generally frustoconical shape for engaging in the core. The bore 48 formed in the core 42 includes, at respective ends, a bottom countersink 48B of shape complementary to that of the base 47A and a top countersink 48A of shape complementary to the engagement end 47B, said centering pin 47 and said bore 48 being arranged so as to encourage annular bearing between the base 47A of the centering pin 47 and the core 42, said annular bearing contributing to controlling the positioning of the core 42 relative to the centering pin 47.

In order to proceed with the unmolding operation, an unmolding pin 49 is provided having one of its ends secured to the bottom soleplate 46, while its other end or leading end 49A is for engaging the bottom countersink 48B of the core 42, and for this purpose presents a shape that allows it to come into abutment against the bottom end 48B of the bore 48. It is thus possible to extract the core 42 from the bottom recess 41 as follows:

the top and bottom recesses 40 and 41 are separated;

then the bottom recess 41 is subjected to vertical translation movement in the direction along which the centering pin 47 extends so as to take the core 42 away from the centering pin 47; and then the subassembly constituted by the bottom recess 41 supporting the core 42 is engaged on the unmolding pin 49 so as to extract the core 42 from the concave shape 41A of the bottom recess 41.

Unmolding proper of the silicone pouch fitting over the surface of the core 42 is performed last. In order to make this operation easier to perform, the core 42 is covered in a uniform layer of Teflon® that is a few micrometers (μm) thick.

Thus, the method of the invention makes it possible, very quickly (cycle time may be about 5 minutes), using a single machine, and using a limited number of operations, to obtain a one-piece intra-gastric balloon presenting wall thickness of great regularity. By way of example, it is possible in this way to make a silicone pouch having nominal wall thickness equal to 0.5 mm with tolerance of less than ±0.08 mm, and possibly being as little as ±0.05 mm.

Numerous shapes of balloon can be made using the method in accordance with the invention, and in particular balloons presenting cells or facets.

SUSCEPTIBILITY OF INDUSTRIAL APPLICATION

Industrial application of the invention lies in making and using intra-gastric balloons for treating obesity.

The invention claimed is:

1. A method of fabricating an intra-gastric balloon (1) for treating obesity, said balloon (1) designed to be implanted in the stomach of a patient in order to reduce the volume of the stomach, said balloon (1) comprising a flexible envelope (2) defining a predetermined inside volume, said flexible envelope (2) being made of an elastomer material, wherein the dimensional tolerance (T) on the nominal thickness ($e_{nom}$) of the envelope lies in the range of 1% to 20%, the method comprising:

injecting an elastomer material into a mold in order to obtain a flexible pouch that is to form the flexible envelope (2) on the balloon (1).

2. The method according to claim 1, wherein, prior to the injection step, the method comprises:

preparing a mold in which a top cavity (40) of generally hemispherical shape is pressed against a bottom cavity (41) likewise of generally hemispherical shape, so as to obtain an inside volume that is substantially spherical in shape, with a spherical core (42) being previously positioned between the two cavities (40, 41), concentrically therewith, the diameter of the core being smaller than the diameter of said inside volume; and wherein the injection step comprising a step of injecting the elastomer material into the space (43) that extends between the core (42) and the cavities (40, 41) so as to obtain a pouch of generally spherical shape that is to form the envelope (2) of the balloon.

* * * * *